United States Patent
Schach et al.

Patent Number: 5,917,036
Date of Patent: Jun. 29, 1999

[54] PROCESS FOR THE PREPARATION OF N-CARBOXYALKYL-3-FLUORO-4-DIALKYLAMINOANILINES

[75] Inventors: Thomas Schach, Gernsheim; Hans Schubert, Kelkheim, both of Germany

[73] Assignee: Clariant GmbH, Frankfurt, Germany

[21] Appl. No.: 09/035,160

[22] Filed: Mar. 5, 1998

[30] Foreign Application Priority Data

Mar. 7, 1997 [DE] Germany .................. 19709443

[51] Int. Cl.⁶ .................................................. C07D 265/30
[52] U.S. Cl. .................... 544/106; 544/358; 546/190; 560/22
[58] Field of Search ............................ 544/106, 358; 546/190; 560/22

[56] References Cited

U.S. PATENT DOCUMENTS

| | | |
|---|---|---|
| 3,515,744 | 6/1970 | Steinbrunn . |
| 3,852,332 | 12/1974 | Cross . |

FOREIGN PATENT DOCUMENTS

| | | |
|---|---|---|
| 812075 | 3/1995 | Germany . |
| WO 95/07271 | 3/1995 | WIPO . |
| WO 95/25106 | 9/1995 | WIPO . |
| WO 96/23788 | 8/1996 | WIPO . |

*Primary Examiner*—Gary Geist
*Assistant Examiner*—Jean F. Vollano
*Attorney, Agent, or Firm*—Scott E. Hanf

[57] ABSTRACT

A process for the preparation of N-carboxyalkyl-3-fluoro-4-dialkylaminoanilines, which comprises reacting, in a first step, 2-chloro-4,5-difluoronitrobenzene of the formula (I)

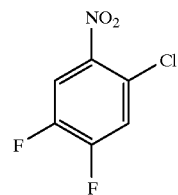

(1)

with a secondary amine of the formula (II) $HNR^1R^2$, in which $R^1$ and $R^2$, independently of one another, are identical or different and are an alkyl radical having from 1 to 10 carbon atoms or, together with the N atom to which they are bonded, form a ring having from 5 to 7 members, in the presence of a water-soluble amine which forms hydrofluorides and hydrochlorides which are liquid at the reaction temperature and work-up temperature or soluble in the reaction mixture, in the presence or absence of a solvent at −10 to 120° C., reducing, in a second step, the reaction mixture containing the 2-chloro-4-dialkylamino-5-fluoronitrobenzene using hydrogen at from 30 to 150° C. and from 1 to 350 bar in the presence of the water-soluble amine and in the presence of a noble-metal catalyst and, in a third step, reacting the reaction mixture containing the 3-fluoro-4-dialkylaminoaniline with a chloroformate of the formula (IV) $ClCO_2R^3$, in which $R^3$ is an alkyl radical having from 1 to 10 carbon atoms or an aralkyl radical having from 7 to 20 carbon atoms, at from 0 to 100° C. in the presence of the water-soluble amine.

15 Claims, No Drawings

PROCESS FOR THE PREPARATION OF N-CARBOXYALKYL-3-FLUORO-4-DIALKYLAMINOANILINES

The present invention relates to a process for the preparation of N-carboxyalkyl-3-fluoro-4-dialkylaminoanilines which is improved compared with the prior art.

N-Carboxyalkyl-3-fluoro-4-dialkylaminoanilines play an important role as intermediates in the preparation of pharmaceuticals (WO-95/25106).

As WO 95/25106 explains, N-carboxybenzyl-3-fluoro-4-piperidinoaniline is used as intermediate in the preparation of oxazolidinone derivatives and pharmaceutical compositions containing these derivatives.

To prepare N-carboxybenzyl-3-fluoro-4-piperidinoaniline (Example 1 of WO 95/25106), 3,4-difluoronitrobenzene is reacted, in a first step, with piperidine in ethyl acetate in the presence of diisopropylethylamine, water is added to the reaction solution, and the ethyl acetate phase is separated off, washed with water and sodium chloride solution and dried over anhydrous sodium sulfate. The solvent is then evaporated off to give the nitro compound (3-fluoro-4-piperidinonitrobenzene). The nitro compound is dissolved in ethyl acetate and hydrogenated in the presence of a palladium catalyst, the catalyst is filtered off and the mixture is evaporated under reduced pressure to give the corresponding amine (3-fluoro-4-piperidinoaniline). In a third step the amine dissolved in tetrahydrofuran is reacted with sodium hydrogencarbonate and a chloroformate and, when the reaction is complete, water is added and the tetrahydrofuran solution is separated off, washed with water and sodium chloride solution and dried over anhydrous sodium sulfate. After the solvent has been evaporated off, the product is purified by column chromatography.

The process for the preparation of N-carboxybenzyl-3-fluoro-4-piperidinoaniline described in WO 95/25106 has several disadvantages. Firstly, only one starting material, namely 3,4-difluoronitrobenzene, can be used and, secondly, 3,4-difluoronitrobenzene is a very expensive product which can only be prepared by a very complex, multi-stage synthesis. Other disadvantages are that the process requires a very large number of individual steps and each intermediate is isolated. Moreover, the individual reaction steps require a significant amount of time, the first stage requiring 2 days and the two other stages each requiring 14 hours.

In view of the above, there is a need to provide a process for the preparation of N-carboxyalkyl-3-fluoro-4-dialkylaminoanilines which avoids the said disadvantages and which can be carried out with an acceptable labor and time expenditure. Moreover, this process should not be limited to the preparation of N-carboxyalkyl-3-fluoro-4-piperidinoanilines, but should make available other compounds from this group of substances.

This object is achieved by a process for the preparation of N-carboxyalkyl-3-fluoro-4-dialkylaminoanilines which comprises reacting, in a first step, 2-chloro-4,5-difluoronitrobenzene of the formula (I)

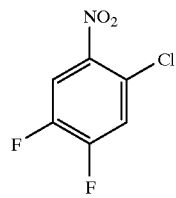

(1)

with a secondary amine of the formula (II) $HNR^1R^2$, in which $R^1$ and $R^2$, independently of one another, are identical or different and are an alkyl radical having from 1 to 10 carbon atoms or, together with the N atom to which they are bonded, form a ring having from 5 to 7 members, in the presence of a water-soluble amine which forms hydrofluorides and hydrochlorides which are liquid at the reaction temperature and work-up temperature or soluble in the reaction mixture, in the presence or absence of a solvent at from −10 to 120° C., reducing, in a second step, the reaction mixture containing the 2-chloro-4-dialkylamino-5-fluoronitrobenzene using hydrogen at from 30 to 150° C. and from 1 to 350 bar in the presence of the water-soluble amine and in the presence of a noble-metal catalyst and, in a third step, reacting the reaction mixture containing the 3-fluoro-4-dialkylaminoaniline with a chloroformate of the formula (IV) $ClCO_2R^3$, in which $R^3$ is an alkyl radical having from 1 to 10 carbon atoms or an aralkyl radical having from 7 to 20 carbon atoms, at from 0 to 100° C. in the presence of the water-soluble amine.

The synthesis strategy of the process according to the invention makes use of the fact that when 2-chloro-4,5-difluoronitrobenzene is used as starting material, all steps can be carried out in the presence of a basic compound. If a suitable basic compound is chosen, it is thus possible to carry out all steps of the process in the presence of one and the same basic compound. If all steps of the synthesis use one and the same basic compound, namely a water-soluble amine, which forms hydrofluorides and hydrochlorides which are liquid under the conditions used for the reaction and work-up, in particular at the reaction temperature and work-up temperature, or which are soluble in the reaction mixture, it is possible to carry out the reaction either in a number of separate steps or else, particularly simply, as a one-pot reaction. Furthermore, 2-chloro-4,5-difluoronitrobenzene, which is essentially easier to prepare than the 3,4-difluorobenzene used in the process of WO 95/25106, is used in particular as a synthesis building block, since the chlorine atom which is not needed can be cleaved off selectively during the synthesis. For the sake of completeness, it should be mentioned that 2,4-dichloro-5-fluoronitrobenzene can be prepared simply by nitration of 2,4-dichlorofluorobenzene.

Another advantage of the process according to the invention is that the desired N-carboxyalkyl-3-fluoro-4-dialkylaminoanilines can be prepared without isolating the intermediates. While it is possible to isolate the corresponding intermediates in order to process them further, it is, however, possible to omit complex intermediary isolation and to carry out the whole process in a one-pot reaction. From an industrial point of view, it may be useful to carry out the one-pot synthesis in a number of reactors or to remove the used catalyst by filtration in the course of the process. All synthesis steps of the process are advantageously carried out without any purification and/or isolation of intermediates, auxiliaries merely being removed, until the desired N-carboxyalkyl-3-fluoro-4-dialkylaminoaniline is isolated.

The novel process for the preparation of N-carboxyalkyl-3-fluoro-4-dialkylaminoanilines is reproduced in simplified form by the following reaction scheme.

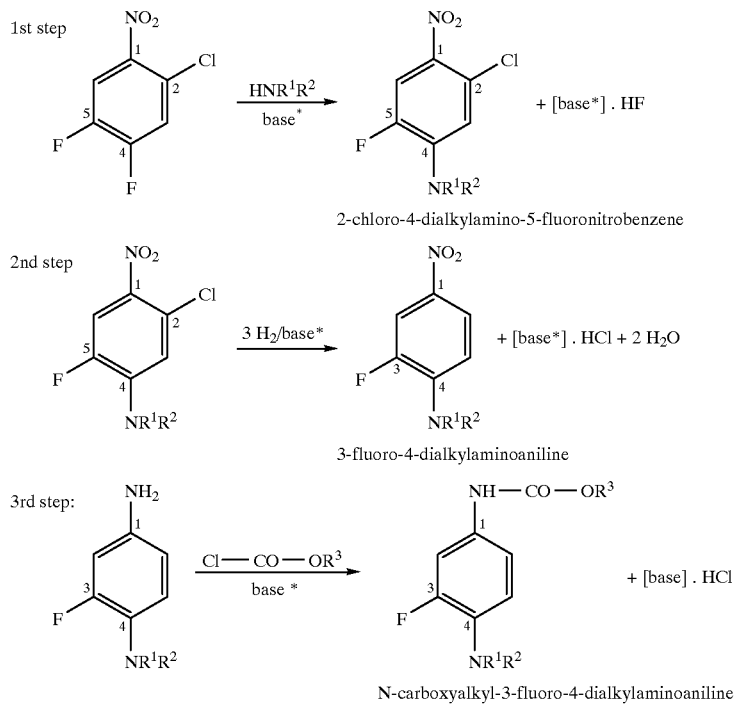

*base = water-soluble amine

As already mentioned above, the fluorine atom in the 4-position in 2-chloro-4,5-difluoronitrobenzene is, in a first step, replaced by an amine radical —$NR^1R^2$ by reaction with the secondary amine of the formula (II) in the presence of a water-soluble amine which forms hydrofluorides and hydrochlorides which are liquid at the reaction temperature and work-up temperature or are soluble in the reaction mixture, as base in the presence or absence of a solvent.

The secondary amine of the formula (II) is dimethylamine, diethylamine, di-n-propylamine, di-i-propylamine, di-n-butylamine, di-i-butylamine, piperidine, morpholine or piperazine, in particular piperidine, morpholine or piperazine, preferably morpholine or piperazine.

Piperidine, morpholine and piperazine are examples of secondary amines of the formula (II) in which $R^1$ and $R^2$, together with the N atom to which they are bonded, form a ring. In each case, this ring has 6 members.

In the reaction of 2-chloro-4,5-difluoronitrobenzene in the first step, the secondary amine serves merely as a reactant, and a water-soluble amine which forms hydrofluorides and hydrochlorides that are soluble (liquid) particularly in the organic phase is added as basic compound.

The water-soluble amine used may be a tertiary water-soluble amine which forms hydrohalides, in particular hydrofluorides and hydrochlorides, which are liquid under the reaction and work-up conditions, particularly at the reaction temperature and work-up temperature, or which are soluble in the reaction mixture. Such tertiary water-soluble amines can be found within the group of alkoxypolyoxy-alkylamines.

A water-soluble amine which can be used successfully is an amine of the formula (III) $NR^3R^4R^5$ in which $R^3$, $R^4$ and $R^5$ are identical or different and are a linear or branched alkyl radical having from 1 to 16, in particular from 1 to 8, preferably from 1 to 4, particularly preferably from 1 to 2, carbon atoms, or an alkoxypolyoxyalkyl radical —$(C_mH_{2m}O)_pR'$ in which R' is an alkyl radical having from 1 to 16, in particular from 1 to 8, preferably from 1 to 4, particularly preferably from 1 to 2, carbon atoms, m is an integer from 1 to 10, in particular from 1 to 5, preferably from 1 to 3, particularly preferably 2 and p is an integer from 1 to 15, in particular from 2 to 10, preferably from 2 to 5, particularly preferably 3 to 4, and at least one of the radicals $R^3$, $R^4$ and $R^5$ is an alkoxypolyoxyalkyl radical —$(C_mH_{2m}O)_pR'$ in which R', m and p are as defined above.

The water-soluble amine used can in many cases be an amine of the formula (III) $NR^3R^4R^5$ in which $R^3$, $R^4$ and $R^5$ are identical or different and at least two of the radicals are an alkoxypolyoxyalkyl radical —$(C_mH_{2m}O)_pR'$, in particular identical alkoxypolyoxyalkyl radicals —$(C_mH_{2m}O)_pR'$.

The water-soluble amine used can, in particular, be an amine of the formula (III) $NR^3R^4R^5$ in which $R^3$, $R^4$ and $R^5$ are identical or different and are an alkoxypolyoxyalkyl radical —$(C_mH_{2m}O)_pR'$.

In many cases, the water-soluble amine is preferably an amine of the formula (III) in which $R^3$, $R^4$ and $R^5$ are identical and are an alkoxypolyoxyalkyl radical —$(C_mH_{2m}O)_pR'$.

Examples of highly suitable water-soluble amines are tri(methyltetraethoxy)amine, tri(butyltetraethoxy)amine, tri(ethyltetraethoxy)amine and di(methyltetraethoxy)methylamine, in particular tri(methyltetraethoxy)amine and di(methyltetraethoxy)methylamine.

From 50 to 500 mol-%, in particular from 90 to 200 mol-%, preferably from 100 to 130 mol-% of water-soluble amine, based on the number of equivalents fluoride or chloride to be eliminated, is used as base. This is the case for the first step, the second step and also the third step in the reaction sequence.

The purpose of the water-soluble amine is to bind the hydrogen fluoride formed in the first stage and the hydrogen chloride formed in each of the second and subsequent stages.

In the reaction of the 2-chloro-4,5-difluoronitrobenzene, it is possible to omit isolating the 2-chloro-4-dialkylamino-5-fluoronitrobenzene and further process directly the reaction mixture produced in the first step. This variant of the process according to the invention is particularly advantageous since it can be carried out particularly easily.

The 2-chloro-4,5-difluoronitrobenzene can be reacted in the presence or absence of a solvent. It is particularly advantageous to minimize the amount of solvent or completely dispense with the use of a solvent if the water-soluble amine is itself used as solvent.

In a large number of cases, preference is given to using the solvent both in the first step and also in the second step. A large number of different solvents are suitable for carrying out the process, including nonpolar solvents, aprotic solvents, dipolar aprotic solvents and polar aprotic solvents.

Without laying claim to completeness, it may be mentioned that the solvent used can be an aliphatic hydrocarbon having from 5 to 25 carbon atoms, an aromatic hydrocarbon having from 6 to 12 carbon atoms, an aliphatic alcohol having from 1 to 12 carbon atoms, a polyalkylene glycol having from 2 to 6 carbon atoms per alkylene, a dialkyl ether having from 2 to 20 carbon atoms per alkyl radical, a polyalkylene glycol dialkyl ether having from 1 to 6 carbon atoms per alkylene, an ester, a dialkylcarboxamide, a dialkyl sulfoxide, a dialkyl sulfone, an imidazolidinone, a pyrrolidone or a mixture thereof.

Solvents which have been used successfully are benzene, toluene, ortho-xylene, meta-xylene, para-xylene, a technical-grade mixture of isomeric xylenes, ethylbenzene, mesitylene, methanol, ethanol, n-propanol, i-propanol, n-butanol, i-butanol, dimethylformamide, diethylformamide, dimethylacetamide, diethylacetamide, dimethyl sulfoxide, dimethyl sulfone, sulfolane, 1,3-dimethylimidazolidin-2-one, N-pyrrolidone or a mixture thereof, in particular toluene, ortho-xylene, meta-xylene, para-xylene, a technical-grade mixture of isomeric xylenes, dimethylformamide, dimethylacetamide, 1,3-dimethylimidazolidin-2-one, alkyl acetates having from 1 to 12 carbon atoms or a mixture thereof, preferably toluene, ortho-xylene, meta-xylene, para-xylene, a technical-grade mixture of isomeric xylenes, methyl acetate, ethyl acetate or butyl acetate.

In a number of cases, it has proven successful, in the first stage of the reaction sequence, to carry out the reaction of a compound of the formula (I) with the secondary amine of the formula (II) at from 0 to 100° C.

In a particular variant, a base is added to the reaction mixture formed in the first step and the water-soluble amine is freed from its hydrofluoride. In particular, an aqueous solution of an alkali metal hydroxide, alkaline earth metal hydroxide or a mixture of these hydroxides, preferably with an aqueous NaOH or KOH solution as base, is added to the reaction mixture formed in he first step.

From 0.8 to 1.5, in particular from 0.95 to 1.05, equivalents of base are usually used per mole of hydrofluoride.

This variant is particularly interesting since it offers a number of advantages. Firstly, the water-soluble amine bound in the form of its hydrofluoride is recovered in a very simple manner, as a result of which, secondly, the quantity of water-soluble amine to be used can be kept low.

Furthermore, removal of the hydrofluoride is not required and removal of the water-soluble amine can also be omitted since the water-soluble amine is also present in the second step of the reaction sequence.

It is of course also possible to omit adding the base to the reaction mixture formed in the first step, to remove the hydrofluoride formed and, if desired, the water-soluble amine, and to work up the hydrofluoride and the water-soluble amine separately.

The reaction mixture containing 2-chloro-4-dialkylamino-5-fluoronitrobenzene originating from the first step or 2-chloro-4-dialkylamino-5-fluoronitrobenzene in isolated form is used in the presence or absence of a solvent in the second step.

The 2-chloro-4-dialkylamino-5-fluoronitrobenzene-containing reaction mixture originating from the first step can be used directly in the second step, i.e. without additional work-up steps.

If 2-chloro-4-dialkylamino-5-fluoronitrobenzene is used in isolated form in the second step, a solvent is normally used. The solvent may be one of the afore-mentioned solvents and/or the water-soluble amine.

In the second step, the 2-chloro-4-dialkylamino-5-fluoronitrobenzene is hydrogenated in the presence of the above-described water-soluble amine as base and a noble-metal catalyst. The nitro group is converted into an $NH_2$ group and at the same time the chlorine in the ortho position relative to the nitro group is cleaved off with the formation of hydrogen chloride. The purpose of the base is to bind the freed hydrogen chloride.

The base used in the second step is usually the same water-soluble amine as used in the first step, namely the tertiary water-soluble amine which forms hydrofluorides or hydrochlorides which are liquid at the reaction temperature and work-up temperature or are soluble in the reaction mixture.

Water-soluble amines which are particularly suitable for the second step of the reaction sequence are tri(methyltetraethoxy)amine, tri-(butyltetramethoxy)amine, tri(ethyltetraethoxy)amine and di-(methyltetraethoxy)methylamine.

In the second step, from 50 to 500 mol-%, in particular from 90 to 200 mol-%, preferably from 100 to 130 mol-% of water-soluble amine, based on the number of equivalents of chloride to be eliminated, are used as base. If the water-soluble amine was used as solvent in a corresponding molar excess in the preceding first reaction step and/or freed from the hydrofluoride formed, it is not necessary to add more in the second reaction step. It must merely be ensured that the reaction mixture, or product, passing into the second step already contains the water-soluble amine in sufficient quantity.

If 2-chloro-4-dialkylamino-5-fluoronitrobenzene is used in isolated form, the water-soluble amine must be added as base in the aforementioned quantity.

The purpose of the base is to bind the hydrogen chloride eliminated during the reductive dechlorination reaction.

The noble-metal catalyst used is a supported palladium catalyst. The noble-metal catalyst contains from 0.1 to 25%, in particular from 0.5 to 10%, preferably from 1.0 to 5.0% by weight of palladium.

The noble-metal catalyst contains activated carbon, calcium carbonate, barium sulfate, pumice, alumina, kieselguhr, silica gel, aluminum oxide or a mixture thereof, in particular activated carbon, kieselguhr, aluminum oxide or a mixture thereof, preferably activated carbon, as support material.

It has proven particularly successful to use a palladium/ activated carbon catalyst as the noble-metal catalyst.

The hydrogenation reaction is carried out in the presence of hydrogen, in a large number of cases at a pressure of from 2 to 100 bar, in particular at a pressure of from 5 to 50 bar, and at a temperature of from 40 to 140° C., in particular from 60 to 130° C.

When carrying out the second step of the reaction sequence, it must be ensured that the solvent used is inert under the hydrogenation conditions. Unsuitable solvents are chlorinated aliphatic or aromatic hydrocarbons since these can react with hydrogen under the reaction conditions. These limitations regarding the solvent apply only to the hydrogenation stage. In order to avoid changing the solvent, it is advantageous to carry out the first step of the reaction sequence using a solvent which is also suitable for the second step of the reaction sequence.

Examples of suitable solvents are the solvents already listed above.

In a particular variant, a base is added to the reaction mixture formed in the second step, optionally after having removed the noble-metal catalyst, and the water-soluble amine is freed from its hydrochloride. In particular, an aqueous solution of an alkali metal hydroxide, alkaline earth metal hydroxide or a mixture of these hydroxides, preferably with an aqueous NaOH or KOH solution as base, is added to the reaction mixture formed in the second reaction step.

From 0.8 to 1.5, in particular from 0.95 to 1.05, equivalents of base are usually used per mole of hydrochloride.

This variant is particularly interesting since it offers a number of advantages. Firstly, the water-soluble amine bound in the form of its hydrochloride is recovered in a very simple manner, as a result of which, secondly, the quantity of water-soluble amine to be used can be kept low. Furthermore, removal of the hydrochloride is not required and removal of the water-soluble amine can also be omitted since the water-soluble amine is also present in the third step of the reaction sequence.

It is of course also possible to omit adding the base to the reaction mixture formed in the second step, to remove the hydrochloride formed and, if desired, the water-soluble amine, and to work up the hydrochloride and the water-soluble amine separately.

The noble-metal catalyst is normally removed from the reaction mixture, for example by filtration, sedimentation or centrifugation. It can be removed prior to or after addition of the base. If the noble-metal catalyst is in the form of a fixed bed, separate removal of the catalyst is not necessary since the catalyst remains in the fixed bed in lumpy form and does not enter the product stream.

The reaction mixture which results from the second step and contains the corresponding 3-fluoro-4-dialkylaminoaniline is reacted, in a third step, with a chloroformate of the formula (IV) Cl—CO—OR$^3$ in the presence of the water-soluble amine to form the corresponding N-carboxyalkyl-3-fluorodiaminoaniline.

The purpose of the water-soluble amine is to bind the hydrogen chloride formed in the third step.

In the third step, from 50 to 500 mol-%, in particular from 90 to 200 mol-%, preferably from 100 to 130 mol-% of water-soluble amine, based on the number of equivalents of fluoride or chloride to be eliminated, is used as base.

If the water-soluble amine was used as solvent in corresponding molar excess in the preceding second reaction step and/or freed from the hydrochloride formed, it is not necessary to add more in the third step of the reaction sequence.

If the water-soluble amine used has already been consumed after the second stage, it is not necessary to add more if the spent water-soluble amine is regenerated by the addition of an alkali metal base or alkaline earth metal base. It is only necessary to add the required molar amount of base, for example sodium hydroxide solution. If necessary, the aqueous phase which forms as a function of the water concentration in the reaction solution can be removed. The subsequent reaction is, however, also carried out in the presence of an aqueous phase.

It must merely be ensured that the reaction mixture passing into the third step already contains the water-soluble amine in sufficient quantity.

The chloroformate of the formula (IV) used is in particular a ClCO$_2$R$^3$ compound in which R$^3$ is an alkyl radical having from 1 to 8, in particular from 1 to 4, carbon atoms or a benzyl radical.

Examples of chloroformates which are suitable for the third stage are methyl chloroformate, ethyl chloroformate, n-propyl chloroformate, i-propyl chloroformate, n-butyl chloroformate, i-butyl chloroformate, benzyl chloroformate, preferably benzyl chloroformate.

In most cases it has proven sufficient to carry out the reaction with the chloroformate at from 10 to 80° C.

In a particular variant, a base is added to the reaction mixture which is formed in the third step and which contains the corresponding N-carboxyalkyl-3-fluoro-4-dialkylaminoaniline, and the water-soluble amine is freed from its hydrochloride. In particular, an aqueous solution of an alkali metal hydroxide, alkaline earth metal hydroxide or a mixture of these hydroxides, preferably with an aqueous NaOH or KOH solution as base, is added to the reaction mixture formed in the third step.

From 0.9 to 2, in particular from 1 to 1.1, equivalents of base are normally used per mole of hydrochloride.

This variant is particularly interesting since it offers a number of advantages. Firstly, the water-soluble amine bound in the form of its hydrochloride is recovered in a very simple manner and, after the synthesis is complete and, if necessary, after it has been worked-up, can be reused in the first step, as a result of which, secondly, the quantity of amine to be used can be kept low and only supplemented by small amounts of fresh water-soluble amine. Furthermore, removal of the hydrochloride is not required. Only the salts which are formed as a result of the water-soluble amine being freed from its hydrofluorides and hydrochlorides (fluorides in the first step, chlorides in the second and third steps) have to be removed.

In some instances, the salts (fluorides and chlorides) form, by the addition of water, in the same way as the water-soluble amine, as an aqueous solution, from which the desired product, namely the corresponding N-carboxyalkyl-3-fluoro-4-dialkylaminoaniline, usually precipitates out as a solid. The desired product is filtered off and purified further by recrystallization. The water-soluble amine and, in some instances, solvent are recovered from the aqueous solution.

If the reaction is carried out in the presence of a water-insoluble solvent, the reaction mixture is formed in solution and can be separated from the aqueous phase by simple phase separation.

When the reaction is complete, the N-carboxyalkyl-3-fluoro-4-dialkylaminoaniline is usually obtained in the solution of all the reactants and auxiliaries added up to that time. The N-carboxyalkyl-3-fluoro-4-dialkylaminoaniline formed can be precipitated as a solid by being dripped into water. This solid can be removed and isolated by filtration and/or extraction with an organic, water-insoluble solvent. The amine used as base dissolves in the water and can be returned to the next batch after regeneration (e.g. freed by NaOH) and removal of the water.

If wished, the desired product can be subjected to further purification, for example by crystallization.

In a particular process variant, the amount of amine consumed in each of the first, second and third steps can be recovered by adding sodium hydroxide solution, so that the required amount of amine for the reaction can be reduced to a minimum of 1 to 2 equivalents of water-soluble amine per mole of starting material.

The process according to the invention can be carried out under reduced pressure, at atmospheric pressure or at superatmospheric pressure.

The invention further relates to the compounds N-carboxymethyl-3-fluoro-4-morpholinoaniline and N-carboxyisobutyl-3-fluoro-4-morpholinoaniline.

EXPERIMENTAL PART

EXAMPLE 1

Preparation of N-Carboxybenzyl-3-fluoro-4-morpholinoaniline 67.1 g (0.77 mol) of morpholine are introduced at 50° C. over the course of one hour into a solution of 135.5 g (0.7 mol) of 2-chloro-4,5-difluoronitrobenzene in 1192 g (2.0 mol) of tri(methyltetraethoxy)amine in a 2000 ml autoclave fitted with gas-dispersion stirrer. The mixture is then stirred for a further 3 hours at the same temperature, 21 g of a palladium/activated carbon catalyst (5% by weight of palladium, 50% water-moist) are added and the autoclave is closed and rendered inert using nitrogen. The reaction temperature is increased to 105° C. and this temperature is maintained at a hydrogen pressure of from 5 to 30 bar until no more hydrogen is absorbed. After the catalyst has been filtered off with suction, 149.3 g (0.88 mol) of benzyl chloroformate (95%) are added to the reaction solution at room temperature. Once addition is complete, the mixture is further stirred for one hour, the solvent is removed under reduced pressure and the residue which remains is introduced into 1000 ml of water. The solid formed is filtered off with suction, washed with water and then recrystallized from methanol.

The amine can then be regenerated from the wastewater which remains by adding sodium hydroxide solution.

All of the reaction steps are carried out under protective gas.
Yield:
173.3 g (0.53 mol) of N-carboxybenzyl-3-fluoro-4-morpholinoaniline, which corresponds to a theoretical yield of 75%, based on 2-chloro-4,5-difluoronitrobenzene used.

EXAMPLE 2

Preparation of N-Carboxybenzyl-3-fluoro-4-morpholinoaniline

A solution of 156.3 g (0.6 mol) of 2-chloro-5-fluoro-4-morpholinonitrobenzene in 763 g (1.3 mol) of tri(methyltetraethoxy)amine and 260 g of toluene, together with 18 g of a palladium/activated carbon catalyst (5% by weight of palladium, 50% water-moist) is introduced at 110° C. into a 2000 ml autoclave fitted with gas-dispersion stirrer. The autoclave is closed and rendered inert using nitrogen, and the mixture is reacted at a reaction temperature of from 95 to 110° C. at a hydrogen pressure of from 5 to 30 bar until no more hydrogen is absorbed. After the catalyst has been filtered off with suction, 128 g (0.71 mol) of benzyl chloroformate (95%) are added to the reaction solution at room temperature. After addition is complete, the mixture is stirred for a further one hour, the solvent is removed under reduced pressure and the residue which remains is introduced into 1000 ml of water. The solid formed is filtered off with suction, washed with water and then recrystallized from methanol.

The amine can then be regenerated from the wastewater which remains by adding sodium hydroxide solution.

All of the reaction steps are carried out under protective gas.
Yield:
156.4 g (0.47 mol) of N-carboxybenzyl-3-fluoro-4-morpholinoaniline, which corresponds to a theoretical yield of 79%, based on 2-chloro-5-fluoro-4-morpholinonitrobenzene used.

EXAMPLE 3

Preparation of N-Carboxybenzyl-3-fluoro-4-morpholinoaniline

A solution of 208.4 g (0.8 mol) of 2-chloro-5-fluoro-4-morpholinonitrobenzene in 611 g (1.04 mol) of tri(methyltetraethoxy)amine and 400 g of butyl acetate, together with 18 g of a palladium/activated carbon catalyst (5% by weight of palladium, 50% water-moist) is introduced at 110° C. into a 2000 ml autoclave fitted with gas-dispersion stirrer. The autoclave is closed and rendered inert using nitrogen and the mixture is reacted at a reaction temperature of from 95 to 110° C. at a hydrogen pressure of from 5 to 30 bar until no more hydrogen is absorbed. After the catalyst has been filtered off with suction, 57.5 g (0.72 mol) of 50% strength NaOH are added to the reaction solution at room temperature, followed by 161.6 g (0.9 mol) of benzyl chloroformate (95%). After the addition is complete, the mixture is stirred for a further one hour at 50° C., a further 72 g (0.9 mol) of 50% strength NaOH and 150 g of water are added and the aqueous phase which forms is separated off. The solvent is then removed under reduced pressure and the residue which remains is introduced into 800 ml of water. The solid formed is filtered off with suction, washed with water and then recrystallized from methanol.

The amine can then be regenerated from the wastewater which remains by adding sodium hydroxide solution.

All of the reaction steps are carried out under protective gas.
Yield:
221.8 g (0.67 mol) of N-carboxybenzyl-3-fluoro-4-morpholinoaniline, which corresponds to a theoretical yield of 84%, based on 2-chloro-5-fluoro-4-morpholinonitrobenzene used.

EXAMPLE 4

Preparation of N-Carboxybenzyl-3-fluoro-4-morpholinoaniline

A suspension of 208.4 g (0.8 mol) of 2-chloro-5-fluoro-4-morpholinonitrobenzene in 516.6 g (0.88 mol) of tri(methyltetraethoxy)amine and 105 g of methanol, together with 18 g of a palladium/activated carbon catalyst (5% by weight of palladium, 50% water-moist) is introduced, at room temperature into a 2000 ml autoclave fitted with gas-dispersion stirrer. The autoclave is closed and rendered inert using nitrogen, and the mixture is reacted at a reaction temperature of from 80 to 100° C. at a hydrogen pressure of from 5 to 30 bar until no more hydrogen is absorbed. After the catalyst has been filtered off with suction, 57.5 g (0.72 mol) of 50% strength NaOH are added to the reaction solution at room temperature, followed by 161.6 g (0.9 mol) of benzyl chloroformate (95% strength). When the addition is complete, the mixture is stirred for a further 15 minutes at 50° C., and 775 g of water and 36 g (0.9 mol) of NaOH are added to the reaction solution/suspension. The solid formed is filtered off with suction, washed with water and then recrystallized from methanol.

Tri(methyltetraethoxy)amine and methanol can then be regenerated from the wastewater which remains by adding an equimolar amount of sodium hydroxide solution.

All of the reaction steps are carried out under protective gas.
Yield:
208.0 g (0.63 mol) of N-carboxybenzyl-3-fluoro-4-morpholinoaniline, which corresponds to a theoretical yield of 78.8%, based on 2-chloro-5-fluoro-4-morpholinonitrobenzene used.

EXAMPLE 5

Preparation of N-Carboxymethyl-3-fluoro-4-morpholinoaniline

A suspension of 208.4 g (0.8 mol) of 2-chloro-5-fluoro-4-morpholinonitrobenzene in 516.6 g (0.88 mol) of tri(methyltetraethoxy)amine and 105 g of methanol, together with 18 g of a palladium/activated carbon catalyst (5% by weight of palladium, 50% water-moist) is introduced at room temperature into a 2000 ml autoclave fitted with gas-dispersion stirrer. The autoclave is closed and rendered inert using nitrogen, and the mixture is reacted at a reaction temperature of from 80 to 100° C. at a hydrogen pressure of from 5 to 30 bar until no more hydrogen is absorbed. After the catalyst has been filtered off with suction, 57.5 g (0.72 mol) of 50% strength NaOH are added to the reaction solution at room temperature, followed by 94.5 g (1.0 mol) of methyl chloroformate (97% strength). When the addition is complete, the mixture is stirred for a further 15 minutes at 50° C., and 775 g of water and 36 g (0.9 mol) of NaOH are added to the reaction solution/suspension. The solid formed is filtered off with suction, washed with water and then recrystallized from methanol.

Tri(methyltetraethoxy)amine and methanol can then be regenerated from the waste water which remains by adding an equimolar amount of sodium hydroxide solution.

All of the reaction steps are carried out under protective gas.
Yield:
150.0 g (0.59 mol) of N-carboxymethyl-3-fluoro-4-morpholinoaniline, which corresponds to a theoretical yield of 73.8%, based on 2-chloro-5-fluoro-4-morpholinonitrobenzene used.

Melting point: 163.5° C. $^1$H-NMR: δ (TMS)=0, (CDCl$_3$): δ=3.86, 3.76, 3.03, 6.74 (NH), 6.86 ($J_{F,H}$=9.0 Hz); 6.98; 7.27 ($J_{F,H}$=13.0 Hz) $^{13}$C-NMR: δ (CDCl$_3$)=77, (CDCl$_3$): δ=51.18 ($J_{F,C}$=3.0 Hz); 52.34; 66.99; 108.02 ($J_{F,C}$=25 Hz); 114.65 ($J_{F,C}$=0 Hz); 119.04 ($J_{F,C}$=4.2 Hz); 133.25 ($J_{F,C}$=10.7 Hz); 135.87 ($J_{F,C}$=9.0 Hz); 154.03 ($J_{F,C}$=0 Hz); 155.71 ($J_{F,C}$=245.8 Hz)

EXAMPLE 6

Preparation of N-Carboxy-i-butyl-3-fluoro-4-morpholinoaniline

A suspension of 192.8 g (0.74 mol) of 2-chloro-5-fluoro-4-morpholinonitrobenzene in 477.9 g (0.81 mol) of tri(methyltetraethoxy)amine and 97.1 g of methanol, together with 16.7 g of a palladium/activated carbon catalyst (5% by weight of palladium, 50% water-moist) is introduced at room temperature into a 2000 ml autoclave fitted with gas-dispersion stirrer. The autoclave is closed and rendered inert using nitrogen, and the mixture is reacted at a reaction temperature of from 80 to 100° C. at a hydrogen pressure of from 5 to 30 bar until no more hydrogen is absorbed. After the catalyst has been filtered off with suction, 54.0 g (0.67 mol) of 50% strength NaOH are added to the reaction solution at room temperature, followed by 114.4 g (0.8 mol) of i-butyl chloroformate (98% strength). When the addition is complete, the mixture is stirred for a further 15 minutes at 50° C., and 775 g of water and 36 g (0.9 mol) of NaOH are added to the reaction solution/suspension. The solid formed is filtered off with suction, washed with water and then recrystallized from methanol.

Tri(methyltetraethoxy)amine and methanol can then be regenerated from the waste water which remains by adding an equimolar amount of sodium hydroxide solution.

All of the reaction steps are carried out under protective gas.
Yield:
159.2 g (0.54 mol) of N-carboxy-i-butyl-3-fluoro-4-morpholinoaniline, which corresponds to a theoretical yield of 72.7%, based on 2-chloro-5-fluoro-4-morpholinonitrobenzene used.

Melting point: 121.0° C. $^1$H-NMR: δ (TMS)=0, (CDCl$_3$): δ=0.96; 1.97; 3.03; 3.86; 3.94; 6.64 (NH), 6.87 ($J_{F,H}$=9.0 Hz); 6.98; 7.28 ($J_{F,H}$=13.0 Hz) $^{13}$C-NMR: δ (CDCl$_3$)=77, (CDCl$_3$): δ=19.0; 27.96; 51.21 ($J_{F,C}$=3.0 Hz); 67.01; 71.48; 107.96 ($J_{F,C}$=25 Hz); 114.53 ($J_{F,C}$=0 Hz); 119.06 ($J_{F,C}$=4.2 Hz); 133.41 ($J_{F,C}$=11.2 Hz); 135.73 ($J_{F,C}$=9.4 Hz); 153.71 ($J_{F,C}$=0 Hz); 155.75 ($J_{F,C}$=245.9 Hz)

We claim:
1. A process for the preparation of N-carboxyalkyl-3-fluoro-4-dialkylaminoanilines, which comprises reacting, in a first step, 2-chloro-4,5-difluoronitrobenzene of the formula (I)

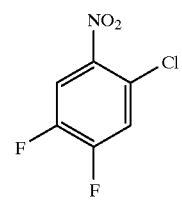

(1)

with a secondary amine of the formula (II) HNR$^1$R$^2$, in which R$^1$ and R$^2$, independently of one another, are identical or different and are an alkyl radical having from 1 to 10 carbon atoms or, together with the N atom to which they are bonded, form a ring having from 5 to 7 members, in the presence of a water-soluble amine which forms hydrofluorides and hydrochlorides which are liquid at the reaction temperature and work-up temperature or soluble in the reaction mixture, in the presence or absence of a solvent at from −10 to 120° C., reducing, in a second step, the reaction mixture containing the 2-chloro-4-dialkylamino-5-fluoronitrobenzene using hydrogen at from 30 to 150° C. and from 1 to 350 bar in the presence of the water-soluble amine and in the presence of a noble-metal catalyst and, in a third step, reacting the reaction mixture containing the 3-fluoro-4-dialkylaminoaniline with a chloroformate of the formula (IV) ClCO$_2$R$^3$, in which R$^3$ is an alkyl radical having from 1 to 10 carbon atoms or an aralkyl radical having from 7 to 20 carbon atoms, at from 0 to 100° C. in the presence of the water-soluble amine.

2. The process as claimed in claim 1, wherein the secondary amine of the formula (II) is dimethylamine, diethylamine, di-n-propylamine, di-i-propylamine, di-n-butylamine, di-i-butylamine, piperidine, morpholine or piperazine.

3. The process as claimed in claim 1, wherein the water-soluble amine used is an amine of the formula (III) $NR^4R^5R^6$, in which $R^4$, $R^5$ and $R^6$ are identical or different, and are an alkyl radical having from 1 to 16 carbon atoms or an alkoxypolyoxyalkyl radical $-(C_mH_{2m}O)_pR'$, in which R' is an alkyl radical having from 1 to 16 carbon atoms, m is an integer from 1 to 10 and p is an integer from 1 to 15, and at least one of the radicals $R^4$, $R^5$ and $R^6$ is the alkoxypolyoxyalkyl radical $-(C_mH_{2m}O)_pR'$.

4. The process as claimed in claim 1, wherein the water-soluble amine used is tri(methyltetraethoxy)amine, tri-(butyltetraethoxy)amine, tri(ethyltetraethoxy)amine or di(methyltetraethoxy)-methylamine.

5. The process as claimed in claim 1, wherein, in the first step, from 50 to 500 mol-% of water-soluble amine, based on the number of equivalents of fluoride to be eliminated, are used.

6. The process as claimed in claim 1, wherein the solvent used is an aliphatic hydrocarbon having from 5 to 25 carbon atoms, an aromatic hydrocarbon having from 6 to 12 carbon atoms, an aliphatic alcohol having from 1 to 12 carbon atoms, a polyalkylene glycol having from 2 to 6 carbon atoms per alkylene, a dialkyl ether having from 2 to 20 carbon atoms per alkyl radical, a polyalkylene glycol dialkyl ether having from 1 to 6 carbon atoms per alkylene, an ester, a dialkylcarbonamide, a nitrile, a dialkyl sulfoxide, a dialkyl sulfone, an imidazolinone, a pyrrolidone or a mixture thereof.

7. The process as claimed in claim 1, wherein a base is added to the reaction mixture formed in the first step and the water-soluble amine is freed from its hydrofluoride.

8. The process as claimed in claim 1, wherein an aqueous solution of an alkali metal hydroxide, alkaline earth metal hydroxide or a mixture of these hydroxides is added as base to the reaction mixture formed in the first step.

9. The process as claimed in claim 1, wherein the 2-chloro-4-dialkylamino-5-fluoronitrobenzene-containing mixture originating from the first step or 2-chloro-4-dialkylamino-5-fluoronitrobenzene in isolated form is used in the second step in the presence or absence of a solvent.

10. The process as claimed in claim 1, wherein, in the second step, from 50 to 500 mol-% of water-soluble amine, based on the number of equivalents of chloride to be eliminated, are used.

11. The process as claimed in claim 1, wherein the noble-metal catalyst used is a supported palladium catalyst.

12. The process as claimed in claim 1, wherein a base is added to the reaction mixture formed in the second step, optionally after having removed the noble-metal catalyst, and the water-soluble amine is freed from its hydrochloride.

13. The process as claimed in claim 1, wherein, in the third step, from 50 to 500 mol-% of water-soluble amine, based on the number of equivalents of chloride to be eliminated, are used.

14. The process as claimed in claim 1, wherein the chloroformate of the formula (IV) is $ClCO_2R^3$, in which $R^3$ is an alkyl radical having from 1 to 8 carbon atoms or a benzyl radical.

15. The process as claimed in claim 1, wherein a base is added to the reaction mixture formed in the third step, and the water-soluble amine is freed from its hydrochloride.

* * * * *